United States Patent [19]
Boatright et al.

[11] Patent Number: 5,471,996
[45] Date of Patent: Dec. 5, 1995

[54] APPARATUS AND METHOD FOR MEASURING ABDUCTION STRENGTH OF A PATIENT'S THUMB

[75] Inventors: James R. Boatright; Richard D. Peindl, both of Charlotte, N.C.

[73] Assignee: Charlotte-Mecklenburg Hospital Authority, Charlotte, N.C.

[21] Appl. No.: 130,108

[22] Filed: Sep. 30, 1993

[51] Int. Cl.[6] .................................................. A62B 5/00
[52] U.S. Cl. ........................ 128/782; 128/774; 33/511; 33/512
[58] Field of Search .................... 128/774, 782, 128/781, 779, 639, 644, 721; 33/511, 512

[56] References Cited

U.S. PATENT DOCUMENTS

| | | | |
|---|---|---|---|
| 3,159,923 | 12/1964 | Daniels et al. | 33/512 |
| 3,918,164 | 11/1975 | Krautmann | 33/511 |
| 4,444,205 | 4/1984 | Jackson | 128/774 X |
| 4,774,966 | 10/1988 | Lemmen | 128/774 |
| 5,249,366 | 10/1993 | Takahashi et al. | 33/512 X |
| 5,263,490 | 11/1993 | Hayes et al. | 128/782 X |
| 5,275,174 | 1/1994 | Cook | 128/774 |

FOREIGN PATENT DOCUMENTS

| | | | |
|---|---|---|---|
| 1473748 | 4/1989 | U.S.S.R. | 128/782 |
| 1704762 | 1/1992 | U.S.S.R. | 128/782 |

*Primary Examiner*—Sam Rimell
*Attorney, Agent, or Firm*—Bell, Seltzer, Park & Gibson

[57] ABSTRACT

An apparatus and method for measuring abduction strength of a patient's thumb. The apparatus includes a frame for receiving the patient's hand thereupon in a longitudinal direction, enabling the thumb of the patient to move freely upwardly and downwardly about the joint at the base of the thumb. A thumb engaging means is pivotally mounted to the frame for engaging the patient's thumb assuring the upward and downward movement thereof. The thumb engaging means is pivotal about a transverse axis. A force transducer means is mounted to the thumb engaging means for detecting the force transmitted between the thumb engaging means and the patient's thumb. The force transducer means produces an output representative of the detected force. A display means is provided for displaying the received output.

33 Claims, 3 Drawing Sheets

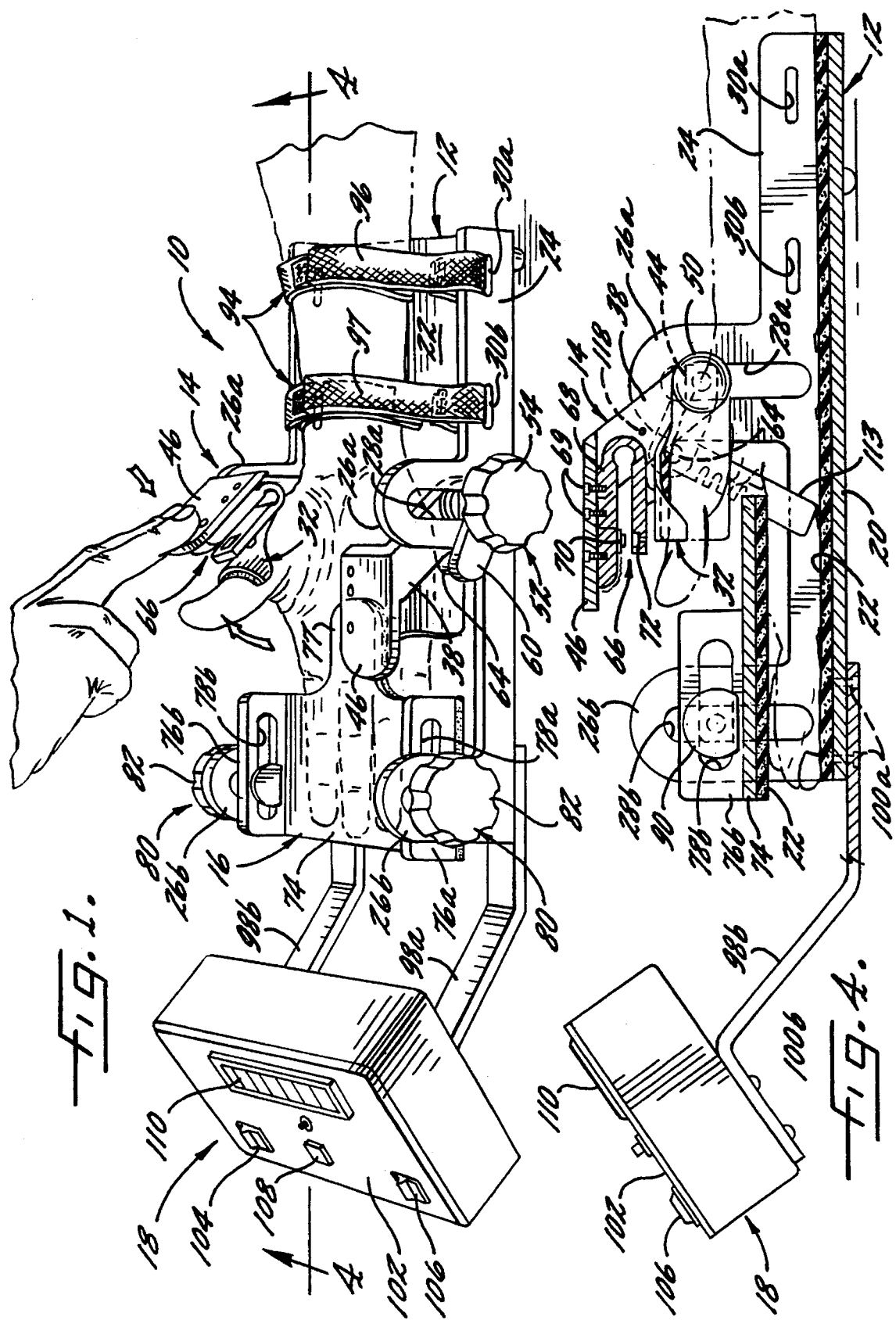

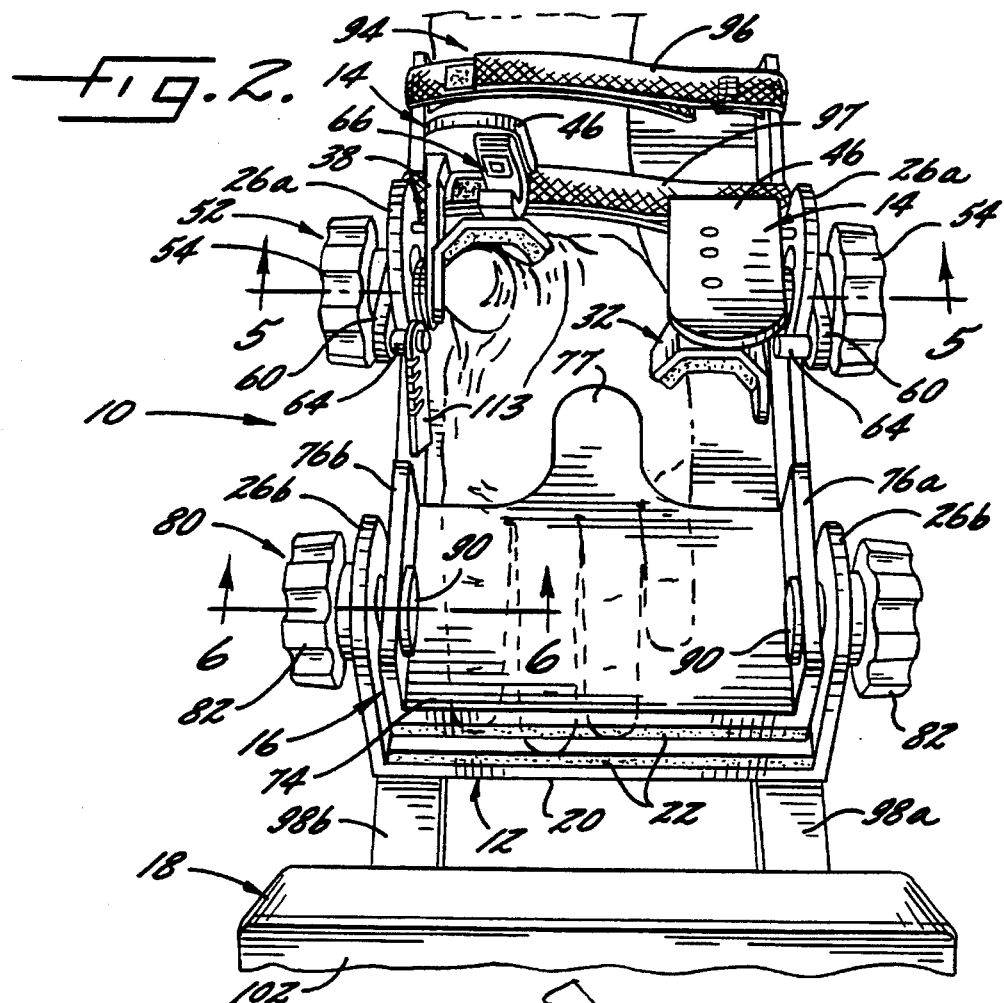
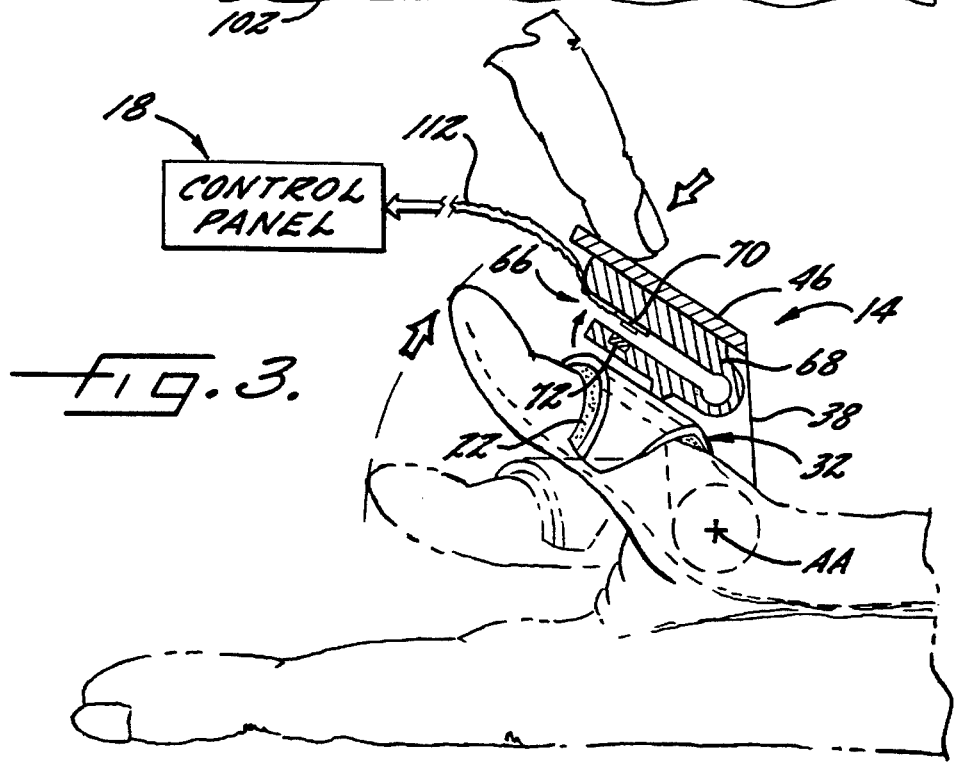

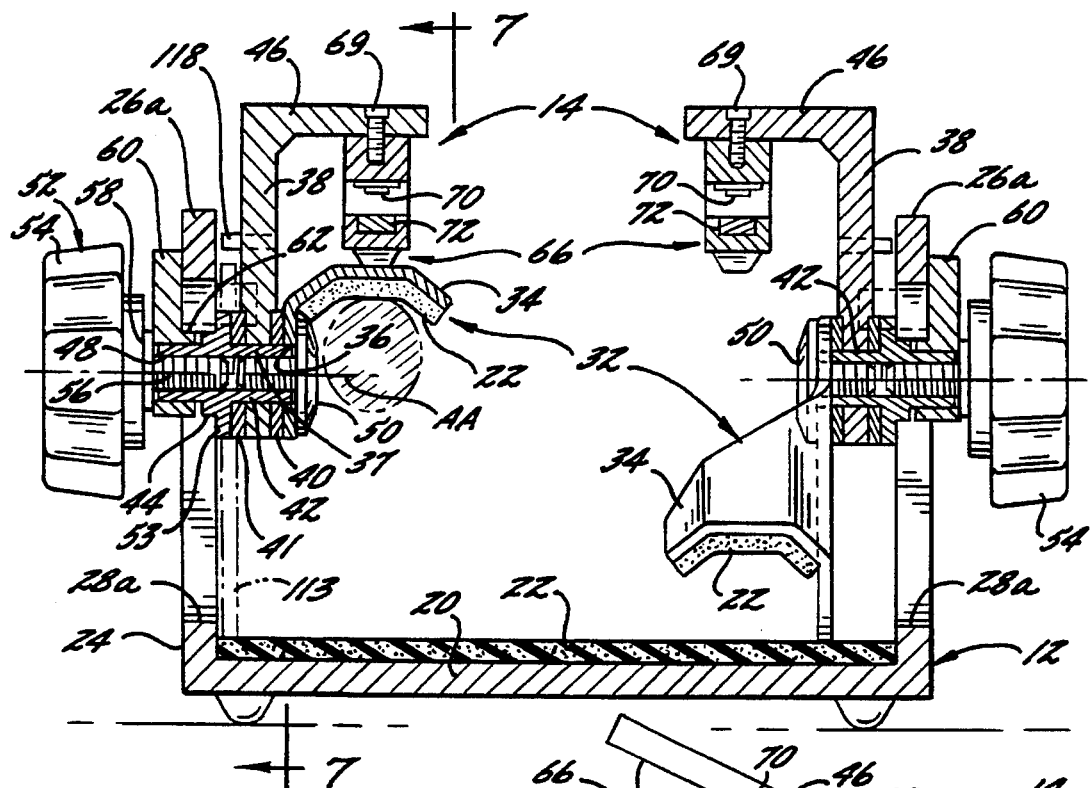
fig.5.
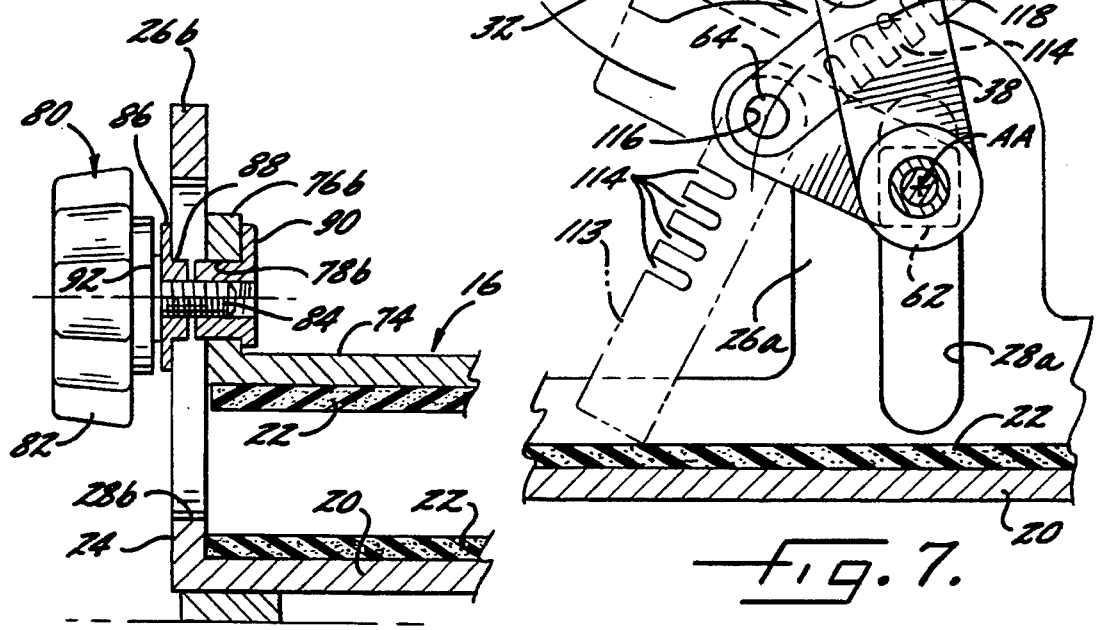
fig.6.
fig.7.

APPARATUS AND METHOD FOR MEASURING ABDUCTION STRENGTH OF A PATIENT'S THUMB

FIELD OF INVENTION

The present invention relates to the field of muscle strength measuring devices, and, more particularly, to an apparatus and method for measuring abduction strength of patient's thumb.

BACKGROUND OF THE INVENTION

The carpal tunnel is a semi-rigid space bound by bone and ligament which runs through the wrist. The median nerve and nine flexor tendons which control movement of the thumb and fingers of the hand go through this tunnel. The abductor pollicis brevis is an intrinsic muscle of the wrist-thumb region of the hand that is exclusively controlled by the median nerve. Injuries and conditions such as Carpal Tunnel Syndrome ("CTS"), some types of neck and elbow injuries as well as other hand disorders affect the innervation of the abductus pollicis brevis. Assessment of this muscle's strength is, thus, an important diagnostic tool in testing for some types of neck and elbow injuries, and for CTS and other hand disorders.

Currently, the strength of the abductor pollicis brevis is subjectively graded by manual testing procedures. Specifically, in conventional diagnostic testing, physicians rely on the patient's history and subjective tests such as the Tinel's Sign, the Phalen's Test, and general sensation. An additional subjective test for measuring thenar abduction strength has been utilized, wherein the physician feels the abduction resistance of the patient's thumb and applies a qualitative rating. A comparison of the affected and unaffected sides provides a basis for the physician's qualitative rating. As with the above-referenced tests, this test does not quantitatively measure anything that can be readily reproduced.

An objective diagnostic test of the median nerve has been developed which measures the conduction status of the median nerve. Slowed conduction along the median nerve is usually interpreted as a sign of nerve damage which may be indicative any of the above-referenced injuries. However, as with other diagnostic tests, nerve conduction studies may have false-positive and false-negative results.

In an article by Robin R. Richards, et al. entitled *Measurement of Wrist, Metacarpophalangeal Joint, and Thumb Extension Strength in a Normal Population*, an objective test is disclosed where the hand positioned with the wrist in a neutral flexion-extension position and the ulnar aspect of the hand firmly positioned on a flat surface of a jig. A measuring device such as a myometer is placed perpendicular to the thumb just distal to the interphlangal joint of the thumb. The patient extends the thumb with maximal force against the myometer head. In this approach the hand is manually restrained to prevent changes in position that might aid in thumb extension. The test disclosed in the Richards, et al. article provides for a quantitative measurement of wrist and thumb extension. The measurement obtained from this test includes muscles not exclusively innervated by the median nerve.

Quantitative measurements of the abductor pollicis brevis strength is necessary for evaluation of procedures effecting the median nerve. Existing devices do not allow rapid, painless, noninvasive and quantitative measurements of thenar abduction resistive strength.

It is important for physicians to be able to quantitatively measure any deterioration of median nerve function over time. The ability to quantitatively measure abduction strength of the abductor pollicis brevis allows the physician to objectively determine whether or not deterioration of the median nerve has occurred. Such a determination assists the physician in evaluating whether or not preliminary treatment of an injury affecting the median nerve is effective or whether an alternative treatment such as an invasive surgical procedure is required. In addition, to perform meaningful treatment outcome studies it is important to be able to compare the pretreatment versus the post treatment strength of the median innervated abductor pollicis brevis muscle. For these studies, qualitative measurement of abduction strength is essential.

SUMMARY OF THE INVENTION

In view of the foregoing background, it is therefore an object of the present invention to provide these and other objects, features and advantages of the present invention by providing an apparatus for measuring abduction strength of a patient's thumb. A primary strength assessment is performed by measuring thenar resistance to forced adduction generally perpendicular to the palm. A frame is provided which has a generally planar base surface which defines a longitudinal direction and a transverse direction. The planar base surface is sized to support the hand of the patient thereupon in the longitudinal direction enabling the thumb of the patient to freely pivot upwardly and downwardly about the joint at the base of the patient's thumb. A thumb engaging means is provided which is pivotally mounted to the frame for engaging the patient's thumb during upward and downward movement thereof. The engagement means is pivotable about a transverse axis generally parallel to the planar base surface and adapted to pass through the joint at the base of the patient's thumb. A force transducer means is mounted to the thumb engaging means for detecting a force transmitted between the thumb engaging means and the thumb of the patient. The force transducer means produces an output representative of the detected force. A display means is provided for displaying the output received.

The invention also includes the thumb engaging means having a thumb cuff for directing, engaging, and supporting the thumb of the patient's hand so that the thumb moves along a predetermined arc about the transverse axis during the upward and downward movement of the thumb in a plane roughly parallel to the longitudinal axis of the hand and roughly perpendicular to the palm. The thumb engagement means also has a lever positioned adjacent to the thumb cuff and has the force transducer means attached to the lever. A mounting means is provided for mounting the thumb engaging means to the frame such that the thumb cuff and the lever are independently pivotable about the transverse axis.

Another feature of the present invention is to provide the force transducer means with a spring element having a generally C-shaped configuration defining a first end and a second end. The spring element in turn has a transducer located in the first end and a magnet located in the second end. In addition, the force transducer means is located between the thumb cuff and the lever.

The ability of the force transducer means to measure changes in the magnetic field in response to deflection of the spring element is an advantage of the present invention.

An additional advantage of the invention is obtained by the inclusion of a second thumb engaging means which is pivotally mounted to the frame to engage the patient's second thumb during upward and downward movement thereof when the patient's second or other hand is inserted into the frame replacing the patient's first hand. The second engaging means is pivotable about a transverse axis generally parallel to the planar base surface and is adapted to pass through the joint at the base of the patient's second thumb. A second force transducer is also provided for detecting a force transmitted between the second thumb engaging means and the second thumb of the patient. The second force transducer means produces an output representative of the detected force. The second thumb engaging means and the second force transducer means are located on the frame in generally parallel alignment with and in opposed relation to the first thumb engaging means and the first force transducer means.

The mounting means for mounting the thumb engaging means to the frame includes as a feature a first adjustment means for selective adjustment of the thumb engaging means along a path which is perpendicular to the planar base surface.

A stop means is provided as another feature of the invention for limiting the pivotal movement of the lever. The stop means is preferably positioned to prevent the lever from forcing the thumb retained within the thumb cuff into contact with the palm of the hand.

A locking means is provided which cooperates with the stop means for selectively locking the lever into a predetermined position along the predetermined arc. This locking means enables the lever to remain stationary under a controlled force.

A first restraining means is provided which is movably affixed to the base for restraining all fingers and palm of the hand therebetween. The first restraining means includes a second adjustment means which can selectively adjust the first restraining means along the longitudinal direction of the planar base surface and selectively adjust the first restraining means along a path perpendicular to the planar base surface to accommodate hands of varying sizes.

A second restraining means is attached to the base for restraining a wrist and a forearm of the hand inserted within the frame.

Another advantage of the present invention is the inclusion of a display means which has a digital panel meter for displaying the output received from the force transducer means in digital form.

The present invention also provides a method of measuring abduction strength of a patient's thumb. The method includes the steps of positioning a hand and a thumb within the apparatus in such a manner that it is possible to locate the hand in the same position in subsequent tests. The hand is then restrained to isolate movement of the thumb against a controlled adductive force applied along a predetermined arc. A quantitative measurement of the resistive strength of the thumb in response to the controlled force applied thereto is obtained, and displayed on the display means.

An object of the present invention is to provide a method of measuring abduction resistance of a patient's thumb. The method includes inserting a hand to be measured into a frame having a first and second restraining means. The first and second restraining means are selectively adjustably attached to the frame and includes a thumb cuff and a lever pivotally and selectively adjustably attached to the frame. The hand is then positioned to ensure the joint at the base of the patient's thumb is located in axial alignment with the thumb cuff. Next, the first restraining means is positioned to restrain both the fingers and the palm of the hand inserted in the frame. The wrist and forearm of the hand to be measured are restrained in the second restraining means. The patient then brings his thumb to the fully abducted position. Next, a controlled force is applied against a lever and the thumb. The force transmitted between the lever and the thumb in response to the controlled force applied thereto is measured. An output produced which is representative of the measured force is displayed on the display means. Since force measurements are always tangent to a predetermined arc related to a fixed pivot, resistive torque about the transverse axis is readily obtained.

Another advantage of the present invention is the ability to compare the output obtained from the test relative to known parameters and to the opposite thumb to determine the existence of CTS and/or other hand disorders.

BRIEF DESCRIPTION OF DRAWINGS

Some of the objects, features and advantages of the present invention having been stated, others will appear as the description proceeds, when taken in conjunction with the accompanying drawings in which;

FIG. 1 is a side view in perspective of the apparatus during performance of a isokinetic assessment of thenar abduction resistance in accordance with the present invention;

FIG. 2 is an end view in perspective showing the apparatus with the patient's hand and thumb properly positioned in accordance with the present invention;

FIG. 3 is a fragmentary view of the thumb engaging means attached to the display means during isokinetic assessment of thenar abduction resistance in accordance with the present invention;

FIG. 4 is a side view partially in cross-section taken along line 4—4 of FIG. 1;

FIG. 5 is an end view in cross-section taken along line 5—5 of FIG. 2;

FIG. 6 is a fragmentary end view taken along line 6—6 of FIG. 2; and

FIG. 7 is a fragmentary view of the locking means limiting pivotal movement of the thumb engaging means during isometric assessment, and showing the locking means in phantom in its position during isokinetic testing, in accordance with the present invention.

DESCRIPTION OF THE ILLUSTRATED EMBODIMENTS

The present invention will now be described more fully hereinafter with reference to the accompanying drawings, in which the preferred embodiment of the invention is shown. This invention may, however, be embodied in many different forms and should not be construed as limited to the embodiments set forth herein. Rather, the illustrated embodiment is provided so that this disclosure will be thorough and complete, and will fully convey the scope of the invention to those skilled in the art. Like numbers refer to like elements throughout.

Referring to FIGS. 1–7, a testing apparatus for measuring abduction resistance strength of a patient's thumb which embodies the features of the present invention is illustrated generally at 10. The apparatus 10 generally includes a frame 12, a thumb engaging means 14, a restraining means 16, and an electronic display means 18.

As best shown in FIGS. 1, 2, 4, and 5, the frame 12 has a generally rectangular configuration. The frame defines a longitudinal direction which, as shown in FIGS. 1, 2, and 4, corresponds to the direction in which a supinated (palm up) hand is placed within the frame 12. The frame 12 also defines a transverse direction, best shown in FIGS. 2 and 5, which is generally perpendicular to the longitudinal direction. The frame has a planar base surface 20 which in this embodiment is covered by a padding 22 made from a rubberized material to provide a comfortable planar base surface for the patient's hand.

Attached to the frame 12 are supports 24a and 24b which extend generally perpendicular to the planar base surface 20 and longitudinally along each side thereof. Support 24a is a mirror image of the other support 24b. For purposes of clarity and consistency, supports 24a and 24b will be referred to collectively as 24 so as to avoid confusion based on the different perspectives shown in FIGS. 1–7. The description of one support 24 is representative of the other support 24.

Support 24 has two generally inverted U-shaped projections 26a and 26b which project upward from and in axial alignment with the support 24. As best shown in FIG. 4, each projection 26a and 26b defines a vertically elongated slot 28a and 28b, respectively. Support 24 also defines a pair of horizontally elongated slots 30a and 30b.

The planar base surface 20 and the supports 24 are cooperatingly sized to comfortably support a patient's hand within the frame 12, while allowing a patient to freely pivot his thumb upwardly away from his palm and downward toward his palm.

As best shown in FIGS. 1, 2, and 5, the thumb engaging means 14 comprises a thumb cuff 32 which has a generally inverted U-shaped end piece 34 which has padding 22 attached thereto. The end piece 34 and padding 22, of the thumb cuff 32 engage, support, and direct the thumb during its upward and downward movement. The thumb cuff 32 defines a first opening 36, at an end opposite the end piece 34.

A lever 38 is located internal to the thumb cuff 32, i.e. closer to the support 24, and separated from the thumb cuff by a first bushing 40, enabling the lever 38 to move independently from the thumb cuff. A second bushing 41 is located internal to the lever adjacent a mounting collar 42 which has a square nut 44 attached thereto and slidably seated within elongated slot 28a. The lever 38 also defines a second opening 37 at one end of the lever. The lever 38 includes a generally U-shaped platform 46 which is mounted to the lever at an end opposite the second opening 37, at an angle approximately 45° as best seen in FIG. 7. The platform 46 provides a generally flat surface when seen in cross section against which a controlled force may be applied in the manner shown in FIG. 1.

The mounting collar 42 is seated within the elongated slot 28a and passes through the second bushing 41, the second opening 37 in the lever 38, the first bushing 40, and the first opening 36 in the thumb cuff 32. The mounting collar 42 defines a threaded internal bore 48 which is adapted to threadedly receive an end cap 50 adjacent the thumb cuff 32 and a first adjustment means, generally indicated at 52, threadedly inserted at an opposite end. The collar 42 also includes a flange 53 at a medial location along its length which engages in the inside surface of the projection 26a.

The first adjustment means 52 in the embodiment shown in FIGS. 1, 2 and 5, has a handle 54 and a threaded bolt 56 projecting generally transverse to the handle 54. Located on the bolt 56 is a washer 58 which engages a stop arm 60 located between the handle 54 and the projection 26a of the support 24.

The stop arm 60 has an integral square nut 62 located at a first end for slidably seating within the elongated slot 28a to prevent the stop arm 60 from pivoting relative thereto. The stop arm also has a stop 64 located at the other end thereof for engaging the lever 38 (note FIGS. 2 and 4) at a predetermined position along a predetermined arc to limit pivotal movement of the lever. The stop 64 thus prevents the lever from forcing the thumb cuff 32 and the thumb beyond the position shown in FIG. 4 and into contact with the palm of the hand under the controlled force.

The threaded bolt 56 and the end cap 50 are in axial alignment with each other and cooperate to form the transverse axis generally indicated at AA about which the thumb cuff 32 and the lever 38 pivot along the predetermined arc.

The first adjustment means 52, through the handle 54 and the threaded bolt 56, is capable of loosening the thumb engaging means 14 relative to the elongated slot 28a to allow the thumb engaging means to move in a vertical direction a predetermined amount within the vertical elongated slot 28a, to ensure that the thumb to be tested is fitted comfortably within the thumb cuff 32. More particularly, the rotation of the handle 54 in a tightening direction causes the projection 26a to be clamped between the lock arm 60 and the flange 53 of the mounting collar 42, to thereby retain the thumb engaging means 14 at a fixed location along the length of the slot 28a. Upon rotation of the handle 54 in the loosening direction, the clamping force is released and the thumb engaging means 14 is free to slide vertically along the slot 28a. The end cap 50 and the threaded bolt 56 of the first adjustment means 52 thus adjustably and pivotally secure the thumb cuff 32 and the lever 38 to the support 24, and fixedly secure the arm means 60 thereto.

A force transducer means generally indicated at 66, is attached to the underside of the platform 46. As best seen in FIGS. 3–5, and 7, the force transducer means 66 comprises a generally C-shaped spring element 68 which has a first end and a second end. The spring element 68 is attached to the platform 46 by conventional fasteners such as bolts 69. The spring element 68 has a known stiffness to enable any deflection to be measured against this known parameter.

A transducer 70 is mounted in one of the either the first end or the second end. In this embodiment, the transducer 70 is mounted in the first end adjacent the platform 46. A rare earth magnet 72 is attached to the other end of the spring element 68. The transducer utilized in this embodiment is a Hall effect transducer. However it is to be understood that an alternative transducer may be substituted therefore, so long as such substituted transducer is sufficiently sensitive to detect changes in the magnetic field caused by movement of the magnet 72 toward the transducer 70 as a result of deflection of the spring element. In addition, it is to be understood that other sensing devices may be utilized to detect the amount of resistive force provided by the thumb and remain within the spirit of the invention.

Deflection of the spring element is caused by a controlled force being applied to the platform 46 of the lever 38. The spring element 68 is attached to the lever 38 between the lever and the thumb cuff 32, such that forced applied to the platform 46 is resisted by the thumb being tested. It is this combination of opposing forces, the controlled force on the lever 38 and the resistance of the thumb against the thumb cuff 32, which causes the spring element 68 to be deflected. Nonferrous materials should be utilized on all components which are in sufficient proximity to the spring element. If ferrous materials are utilized in the proximity of the magnetic field, they may negatively effect the magnet field produced between the transducer 70 and the magnet 72.

A first restraining means 16 best shown in FIGS. 1, 2, and 4, has a generally rectangular configuration and comprises a generally planar base plate 74 with a pair of side members 76a and 76b projecting generally upwardly by therefrom. The base plate includes a generally u-shaped extension 77 which overlies and selectively restrains the palm of the hand. Each side member 76a and 76b (which are a mirror image of the other), defines a longitudinally extending slot 78a and 78b respectively, which cooperates with a second adjustment means generally indicated at 80. Padding 22 is located on the underside of the base plate where the first restraining means comes into contact with the hand.

The second adjustment means 80 best seen in FIG. 6, has a handle 82 with a threaded bolt 84 projecting transversely therefrom. A bushing 86 has a square nut 88 integrally mounted thereto and slideably seated within the elongated slot 28b. A fastening block 90 has a square nut integrally mounted thereto to cooperate with the horizontal elongated slot 78b in the side member 76b. A washer 92 is located on the threaded bolt 84 between the handle 82 and the bushing 86. The threaded bolt passes through the bushing 86, the projection 26b, the side member 76b, and threadingly engages the fastening block 90 to adjustably secure the first restraining means 16 to the frame 12.

It is to be understood that the thumb engaging means 14, the force transducer arm 66, the first adjustment means 52, the stop means 60, and the second adjustment means 80, and their respective components, are also attached to support 24b. These above described elements and their respective components have the same function, operate in the same manner, for the same reason as their respective counterparts previously described. The sole difference between those elements attached to support 24a and those elements attached to support 24b, is that those elements attached to support 24a cooperate with the thumb of the patient's left hand and those elements attached to support 24b cooperate with the thumb of the patient's right hand. Or in the case of the first adjustment means 52, the second adjustment means 80, and the first restraining means 16, these elements and their respective components cooperate with whichever of the patient's hands is inserted into the frame. For the sake of brevity, and because they have been previously described in detail with reference to support 24a, those elements and their respective components attached to support 24b will not be repeated.

To accommodate hands of varying sizes, the first restraining means 16 is adjustable in both the longitudinal direction within the horizontal elongated slot 78 and in the vertical direction within the vertical slot 28b. The handle 82 is loosened to allow the first restraining means to move in both directions to the desired location to restrain all fingers of the hand to ensure that the thumb is in axial alignment with the thumb cuff 32. Then the handle is tightened securing the first restraining means 16 in position.

A second restraining means 94, as may best be seen in FIGS. 1 and 2, includes at least one but preferably two restraining straps 96 and 97 to restrain the forearm and wrist, respectively. In this embodiment, fabric straps having a Velcro® closure mechanism are used. It is to be understood that any number of alternative methods may be utilized to secure the wrist and forearm in the desired position and still remain within the spirit of the invention. The purpose of restraining the wrist and forearm of the hand that is being tested is to isolate movement of the thumb and to minimize the possibility of the patient obtaining a mechanical advantage which would have a negative effect on the results obtained.

Although not shown, an alternative embodiment of the invention could include an additional restraining means for restraining the forefingers in a lateral direction to prevent them from spreading during the testing procedure, and to prevent the hand from laterally sliding between the supports 24a, 24b. Thus the desired alignment between the patient's thumb and the thumb cuff 32 as best seen in FIG. 2, may be maintained.

A pair of support brackets 98a and 98b, are fastened at one end to the bottom of the frame 12 by conventional fasteners such as bolts 100a. Bolts 100b also secure the opposite end of the support brackets 98a and 98b to the electronic display means 18. As best shown in FIGS. 1 and 4, the display means comprises an electronic display panel 102 which has an ON/OFF switch 104, a reset button 106, a peak load activation switch 108, and a digital display panel 110. An electronic cable 112 (shown in FIG. 3) connects the force transducer means 66 to the display means 18.

The transducer 70, provides an analog voltage proportional to the change in the magnetic field resulting from the deflection in the spring element 68. This output signal from the transducer 70 is then delivered to an electronic circuit which amplifies and filters the signal. The signal is also processed by means of a peak detect circuit and then the output is displayed in digital form on the digital display panel 110. It is to be understood that the circuitry for converting the detection of change in the magnetic field to a digital output on the display panel 110 is conventional and well known to those skilled in the art.

As an alternative to the digital display, it is possible to utilize other known forms of obtaining and displaying the output without the use of electronic equipment, such as a mechanical tension spring displaying the resistive force applied by the thumb on an analog meter.

A locking plate 113, best shown in FIG. 7, has a plurality of notches 114 located on one side of the locking plate 13. The locking plate 113 also defines an aperture 16 adapted to fit over the stop 64. The locking plate fits onto the stop 64 such that the locking plate may be pivoted toward and engage a pin 118 located on the lever 38 in one of the notches 114. since the arm 60 is fixed against rotation about the transverse axis AA, the cooperation between the pin 118 and the notches 114 in the locking plate prevents the lever from moving in either direction along the predetermined arc. The result is that the lever may be locked into a desired position, against which the thumb cuff 32 can exert a force for purposes of isometric testing. The existence of a number of notches 14 on the locking plate 113 enables the lever to be locked into a number of different positions. The locking means 113 is easily removed from the stop and the pin 18 to allow the apparatus to be utilized for isokinetic testing.

In operation, the individual inserts his/her supinated hand into the frame 12 in a longitudinal direction until the first joint at the base of the thumb is in axial alignment with the thumb cuff 32. The first restraining means 16 is then adjusted as needed in both the longitudinal and transverse directions by the second adjustment means 80, to secure all fingers and the palm of the hand. The thumb cuff 32 is then adjusted by the first adjustment means 52 until the end piece 34 of the thumb cuff 32 securely engages the thumb to be tested. The second restraining means 94, using the forearm restraint 96 and the wrist restrain 97, then restrains both the forearm and the wrist, respectively, of the hand inserted into the frame 12.

For isometric testing, the locking plate 113 is engaged, locking the lever 38 in the desired predetermined position. The patient then applies force with his/her thumb located in the thumb cuff 32 against the fixed lever 38, causing the spring element 68 of the peak force transducer means 66 to deflect. The transducer detects either the force applied and/or the duration and range of the force applied. The display panel then displays the desired information on the digital display panel 110.

For isokinetic testing, the locking plate 113 is not utilized, this allows the lever 38 to travel along the predetermined arc. Upon a command from either the patient or the tester, a controlled force is applied to the platform 46 of the lever 38. This controlled force may be manually applied by the tester or may be applied by use of a torsion spring or the like (not shown) at a predetermined force. For purposes of this embodiment, the controlled force is applied to the platform 46 manually. The patient upon a command is instructed to fully abduct his/her thumb and to resist with his/her thumb engaging the thumb cuff 32, against the predetermined controlled force applied to the lever 38, throughout the predetermined arc, until the lever 38 contacts the stop 64 on the stop arm 60. Again the transducer 70 detects the amount of deflection of the spring element 68 which represents the resistive force applied by the thumb. This output is again displayed on the digital display panel 110, in whatever form desired, i.e. peak load and/or range of force and/or time of force applied.

The nature of the tests which may be performed on this apparatus 10 are extremely varied. For example, isometric tests may be performed at a number of different angles, due to the number of notches 114 in the locking plate 113. The isometric tests may also be performed for varying lengths of time. Isokinetic tests may vary the size of the predetermined arc, the rate at which the controlled force is applied, the speed at which the lever moves along the predetermined arc, the type of force applied as well as the length of time over which the force is applied.

Many modifications and other embodiments of the invention will come to mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. An apparatus for measuring abduction strength of a patient's thumb, said apparatus comprising:

a frame having a generally planar base surface defining a longitudinal direction and a transverse direction, said planar base surface defining a longitudinal direction and a transverse direction, said planar base surface being sized to support the hand of the patient thereupon in the longitudinal direction enabling the thumb of the patient to freely pivot upwardly and downwardly about the joint at the base of the patient's thumb;

thumb engaging means pivotally mounted to said frame for engaging the patient's thumb during upward and downward movement thereof, said thumb engaging means being pivotable only about a transverse axis generally parallel to said planar base surface and adapted to pass through the joint at the base of the patient's thumb;

force transducer means mounted to said thumb engaging means for detecting a force transmitted between said thumb engaging means and the thumb of the patient, said force transducer means producing an output representative of the detected force; and display means for displaying said output.

2. The apparatus as defined in claim 1 wherein said thumb engaging means comprises a thumb cuff for directing, engaging, and supporting the thumb of the patient's hand so that the thumb moves along a predetermined arc about said transverse axis during the upward and downward movement of the thumb, and a lever positioned adjacent said thumb cuff and having said force transducer means attached thereto, and mounting means for mounting said thumb engaging means to said frame such that said thumb cuff and said lever are independently pivotable about said transverse axis.

3. An apparatus as defined in claim 2 wherein said force transducer means comprises a spring element having a generally C-shaped configuration and defining a first end and an opposite second end, a transducer located in one of said first end and said second end and a magnet located in the other of said first end and said second end.

4. An apparatus as defined in claim 3 wherein said transducer measures changes in the magnetic field of said magnet in response to deflection of said spring element.

5. An apparatus as defined in claim 3 wherein said force transducer means is mounted to said lever and is located between said thumb cuff and said lever.

6. An apparatus as defined in claim 2 further comprising a second thumb engaging means pivotally mounted to said frame for engaging the patient's second thumb during upward and downward movement thereof when the patient's second hand is inserted into said frame to replace the patient's first hand, said second thumb engaging means being pivotable about a transverse axis generally parallel to said planar base surface and adapted to pass through the joint at the base of the patient's second thumb;

second force transducer means mounted to said second thumb engaging means for detecting a force transmitted between said second thumb engaging means and the patient's second thumb, said second force transducer means producing an output representative of the detected force; and display means for displaying said output of said second force transducer means; and wherein said second thumb engaging means and said second force transducer means are located on said frame in generally parallel alignment with and in opposed relation to said first mentioned thumb engaging means and said first mentioned force transducer means.

7. The apparatus as defined in claim 2 wherein said mounting means for mounting said thumb engaging means to said frame includes first adjustment means for selective adjustment of said transverse axis along a path which is substantially perpendicular to said planar base surface.

8. An apparatus as defined in claim 2 further comprising stop means for limiting the pivotal movement of said lever about said transverse axis.

9. An apparatus as defined in claim 8 wherein said stop means is positioned to prevent said lever from forcing the thumb retained within said thumb cuff into contact with the palm of the hand.

10. An apparatus as defined in claim 8 further comprising locking means for selectively locking said lever into a predetermined position along its pivotal movement, enabling said lever to remain stationary under a controlled force.

11. An apparatus as defined in claim 1 further comprising first restraining means movably affixed to said frame for restraining all fingers of the patient's hand therebetween.

12. An apparatus as defined in claim 11 wherein said first restraining means includes an extension for restraining the palm of the patient's hand between said extension and said base surface.

13. An apparatus as defined in claim 11 wherein said first restraining means includes second adjustment means for selectively adjusting said first restraining means along the longitudinal direction of said planar base surface and selectively adjusting said first restraining means along a path perpendicular to said planar base surface to accommodate hands of varying sizes.

14. An apparatus as defined in claim 11 further comprising padding located on said planar base surface, said thumb engaging means, and said restraining means, where said planar base surface, said thumb engaging means, and said restraining means contact the patient's hand.

15. An apparatus as defined in claim 11 further comprising second restraining means attached to said frame for restraining a wrist and a forearm of the hand inserted within the frame.

16. An apparatus as defined in claim 15 wherein said second restraining means comprises at least one selectively releasable strap.

17. An apparatus as defined in claim 1 wherein said display means comprises a digital panel meter for displaying said output received from said force transducer means in digital form.

18. An apparatus for measuring abduction resistance of a patient's thumb, said apparatus comprising:
 a frame having a generally planar base surface defining a longitudinal direction and a transverse direction, said base being sized to support the hand of a patient thereupon, enabling the thumb to pivot freely upwardly and downwardly about the joint at the base of the patient's thumb;
 first restraining means attached to said frame for restraining all fingers of the patient's hand in a desired position;
 second restraining means attached to said frame for restraining the wrist and forearm of the patient's hand longitudinally inserted within said frame;
 thumb engaging means pivotally mounted to said frame for engaging the patient's thumb during upward and downward movement thereof, said thumb engaging means being pivotable about a transverse axis generally parallel to said planar base surface and adapted to pass through the joint at the base of the patient's thumb;
 force transducer means mounted to said thumb engaging means for detecting a force transmitted between said thumb engaging means and the thumb and for producing an output representative of the detected force; and
 display means for displaying said output.

19. The apparatus as defined in claim 18 wherein said thumb engaging means comprises a thumb cuff for directing, engaging, and supporting the thumb of the patient's hand so that the thumb moves along a predetermined arc about said transverse axis during the upward and downward movement of the thumb, and a lever positioned adjacent said thumb cuff and having said force transducer means attached thereto, and mounting means for mounting said thumb engaging means to said frame such that said thumb cuff and said lever are independently pivotable about said transverse axis.

20. The apparatus as defined in claim 19 wherein said mounting means for mounting said thumb engaging means to said frame includes first adjustment means for selective adjustment of said transverse axis along a path which is substantially perpendicular to said planar surface.

21. An apparatus as defined in claim 19 wherein said force transducer means is mounted to said lever and is located between said thumb cuff and said lever.

22. An apparatus as defined in claim 19 wherein said force transducer means comprises a spring element having a generally C-shaped configuration and defining a first end and an opposite second end, and a transducer located in said first end and a magnet located in said second end.

23. An apparatus as defined in claim 22 wherein said spring element has a known stiffness.

24. An apparatus as defined in claim 22 wherein said transducer measures changes in the magnetic field in response to deflection of said spring element.

25. An apparatus as defined in claim 19 further comprising stop means for limiting the pivotal movement of said lever about said transverse axis.

26. An apparatus as defined in claim 19 wherein said stop means is positioned to prevent said lever from forcing the thumb retained within said thumb cuff into contact with the palm of the patient's hand.

27. An apparatus as defined in claim 26 further comprising locking means for selectively locking said lever into a predetermined position along its pivotal movement enabling said lever to remain stationary under a controlled force.

28. An apparatus as defined in claim 19 further comprising a second thumb engaging means pivotally mounted to said frame for engaging the patient's second thumb during upward and downward movement thereof when the patient's second hand is inserted into said frame to replace the patient's first hand, said second thumb engaging means being pivotable about a transverse axis generally parallel to said base and adapted to pass through the joint at the base of the patient's second thumb;
 second force transducer means mounted to said second thumb engaging means for detecting a force transmitted between said second thumb engaging means and the patient's second thumb, said second force transducer means producing an output representative of the detected force; and
 display means for displaying said output of said second force transducer means; and wherein said second thumb engaging means and said second force transducer means are located on said frame in generally parallel alignment with and in opposed relation to said first mentioned thumb engaging means and said first mentioned force transducer means.

29. An apparatus as defined in claim 18 wherein said first restraining means includes second adjustment means for selectively adjusting said first restraining means along said longitudinal direction of said planar base surface and selectively adjusting said first restraining means along a path perpendicular to said planar base surface to accommodate hands of varying sizes.

30. An apparatus as in claim 29 wherein said first restraining means includes an extension for restraining the palm of the hand between said extension and said base surface.

31. An apparatus as defined in claim 18 wherein said second restraining means comprises at least one selectively releasable strap.

32. An apparatus as defined in claim 18 further comprising padding located on said base, said thumb engagement means, and said first and second restraining means, where said base, said thumb engagement means, and said first and second restraining means contact the patient's hand.

33. An apparatus as defined in claim 18 wherein said display means comprises a digital panel meter for displaying said output received from said force transducer means in digital form.

* * * * *

UNITED STATES PATENT AND TRADEMARK OFFICE
CERTIFICATE OF CORRECTION

PATENT NO. : 5,471,996  
DATED : December 5, 1995  
INVENTOR(S) : Boatright et al.

It is certified that error appears in the above-indentified patent and that said Letters Patent is hereby corrected as shown below:

Column 5, line 44, after "cuff" insert -- 32. --.

Column 5, line 45, after "lever" insert -- 38 --.

Column 8, line 31, "110" should be -- 110 --.

Column 8, line 33, "110" should be -- 110 --.

Column 8, line 42, "13" should be -- 113 --.

Column 8, line 43, "16" should be -- 116 --.

Column 8, line 49, after "plate" insert -- 113 --.

Column 8, line 54, "14" should be -- 114 --.

Column 8, line 56, after "stop" insert -- 64 --.

Column 8, line 56, "18" should be -- 118 --.

Column 9, lines 56-57, delete "defining a longitudinal direction and a transverse direction, said planar base surface".

UNITED STATES PATENT AND TRADEMARK OFFICE
CERTIFICATE OF CORRECTION

PATENT NO. : 5,471,996
DATED : December 5, 1995
INVENTOR(S) : Boatright et al.

It is certified that error appears in the above-indentified patent and that said Letters Patent is hereby corrected as shown below:

Column 12, line 59, after "as" insert -- defined --.

Signed and Sealed this

Thirtieth Day of July, 1996

Attest:

BRUCE LEHMAN

*Attesting Officer*   *Commissioner of Patents and Trademarks*